United States Defensive Publication [19] (H) [11] T972,001

Weber, II et al. [43] Jul. 4, 1978

[54] NOVEL UV ABSORBING COMPOUNDS AND PHOTOGRAPHIC ELEMENTS CONTAINING UV ABSORBING COMPOUNDS

[75] Inventors: Wayne Woodrow Weber, II; Donald Warren Heseltine, both of Rochester, N.Y.

[73] Assignee: Eastman Kodak Company, Rochester, N.Y.

[21] Appl. No.: 762,356

[22] Filed: Jan. 25, 1977

Related U.S. Application Data

[60] Division of Ser. No. 641,788, Dec. 18, 1975, which is a continuation-in-part of Ser. No. 506,913, Sep. 17, 1974, abandoned.

[51] Int. Cl.[2] ..... C07C 87/24; C07D 223/02; C07D 241/02; C07D 295/20

[52] U.S. Cl. ..... 542/469; 260/239 BF; 260/268 CN; 260/465.5 R; 544/163

[57] ABSTRACT

1-Amino-4-cyano-1,3-butadiene compounds of the formula

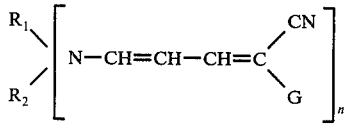

wherein $n$ is 1 or 2; when $n$ is 1, $R_1$ and $R_2$ are the same or different and represent hydrogen, alkyl including substituted alkyl, aryl including substituted aryl or cyclic alkyl groups, except that both $R_1$ and $R_2$ cannot be hydrogen, or taken together $R_1$ and $R_2$ represent the elements necessary to complete a cyclic amino group and, when $n$ is 2, at least one of $R_1$ and $R_2$ is alkylene or arylene; G represents an electron withdrawing group. The compounds are especially useful in photographic elements as UV absorbers. Particularly useful UV absorbers are 3-dibutylaminoallylidenemalononitrile, 3-dihexylaminoallylidenemalononitrile, 3-tert-butylaminoallylidenemalononitrile, 3-diisobutylaminoallylidenemalononitrile, 3-di-sec-butylaminoallylidenemalononitrile, 3-hexahydroazepinoallylidenemalononitrile, 3-N(n-butyl)-N-cyanomethyl aminoallylidenemalononitrile, 3[N,N-bis-(2,2-diethoxyethyl)amino]allylidenemalononitrile, 3(N-methyl-N-cyanomethyl)aminoallylidenemalononitrile, 1,4-piperazino bis(allylidenemalononitrile), N,N-diethyl-N,N-di-(4,4-dicyanobutadienyl)-1,6-diaminohexane, 3-[N,N-bis(2-cyanoethyl)amino]allylidenemalononitrile, 3-morpholinoallylidene methylsulfonylacetonitrile, 3-morpholinoallylidene 4-tert-butylphenylsulfonylacetonitrile, 3-piperazinoallylidene 4-tert-butylphenylsulfonylacetonitrile and 3-N-methylpiperazinoallylidene 4-tert-butylphenylsulfonylacetonitrile.

6 Claims, No Sheets Drawing,

33 Pages Specification

The file of this unexamined application may be inspected and copies thereof may be purchased (849 O.G. 1221, Apr. 9, 1968).